United States Patent [19]

Modrich et al.

[11] Patent Number: 5,459,039
[45] Date of Patent: Oct. 17, 1995

[54] METHODS FOR MAPPING GENETIC MUTATIONS

[75] Inventors: Paul Modrich, Durham, N.C.; Shin-San Su, Cambridge, Mass.; Karin G. Au; Robert S. Lahue, both of Durham, N.C.

[73] Assignee: Duke University, Durham, N.C.

[21] Appl. No.: 334,612

[22] Filed: Mar. 18, 1994

Related U.S. Application Data

[63] Continuation of Ser. No. 2,529, Jan. 11, 1993, abandoned, which is a continuation of Ser. No. 350,983, May 12, 1989, abandoned.

[51] Int. Cl.⁶ ..................................................... C12Q 1/68
[52] U.S. Cl. .................................. 435/6; 935/77; 935/78; 436/501
[58] Field of Search ........................... 435/6; 436/501; 935/77, 78

[56] References Cited

U.S. PATENT DOCUMENTS 4,794,075  12/1988  Ford et al. ................................. 435/6

FOREIGN PATENT DOCUMENTS 9322457  11/1993  WIPO.

OTHER PUBLICATIONS

Lu et al. Cold Spring Harbor Symp. Quant. Biol. 49, 589–96 (1984).
Lu et al. Cell, vol. 54, 805–812, Sep. 9, 1988.
Adams et al. The Biodchemistry of Nucleic Acids Chapman & Hall, 1986, pp. 221–223.
Hennighausen et al. Guide to Molec. Cloning Tech, Berger et al. editors Acidemic Press, Inc. 1987 pp. 721–735.
Quinones et al. Mol Gen Genet. (1988) 211: 106–112.
Su et al. Proc Natl Acad Sci USA vol 83 pp. 5057–5061 Jul. 1986.
Cotton et al. Proc Natl Acad Sci. USA vol. 85 pp. 4397–4401 Jun. 1988.
Modrich, "Molecular Mechanisms of DNA– Protein Interaction", 1986, NIH Grant, Abstract (Source: CRISP).
Modrich, "Molecular Mechanisms of DNA– Protein Interaction", 1987, NIH Grant, Abstract (Source: CRISP).
Modrich, "Molecular Mechanisms of DNA – Protein Interaction", 1988, NIH Grant, Abstract (Source: CRISP).
Modrich, "Molecular Mehcanisms of DNA – Protein Interaction", 1989, NIH Grant, Abstract (Source: CRISP).
Modrich, "Molecular Mechanisms of DNA – Protein Interaction", 1990, NIH Grant, Abstract (Source: CRISP).
Modrich, "Molecular Mechanisms of DNA – Protein Interaction", 1991, NIH Grant, Abstract (Source: CRISP).
Modrich, "Molecular Mechanisms of DNA – Protein Interaction", 1992, NIH Grant, Abstract (Source: CRISP).
Modrich, "Molecular Mechanisms of DNA – Protein Interaction", 1993, NIH Grant, Abstract (Source: CRISP).
Modrich, "Enzymology of Eukaryotic DNA Mismatch Repair", 1991, NIH Grant, Abstract (Source: CRISP).
Modrich, "Enzymology of Eukaryotic DNA Mismatch Repair", 1992, NIH Grant, Abstract (Source: CRISP).
Modrich, "Enzymology of Eukaryotic DNA Misematch Repair", 1993, NIH Grant, Abstract (Source: CRISP).
Su et al, Mispair Specificity of Methyl–directed DNA Mismatch in Vitro, The Journal of Biological Chemistry, 1988, pp. 6829–6835.

*Primary Examiner*—Margaret Parr
*Assistant Examiner*—Carla Myers
*Attorney, Agent, or Firm*—Lyon & Lyon

[57] ABSTRACT

The present invention relates to a method for detecting base sequence differences within homologous regions of two DNA molecules comprising the steps of contacting at least one strand of the first DNA molecule with the complementary strand of the second DNA molecule under conditions such that base pairing occurs, contacting the resulting DNA duplexes with a protein that recognizes substantially all base pair mismatches under conditions such that the protein forms specific complexes with its cognate mispairs, and detecting the resulting DNA:protein complexes by a suitable analytical method. Also disclosed are protein components of DNA mismatch correction systems and the use of these components in methods for genetic mapping.

6 Claims, 3 Drawing Sheets

V 5'-AAGCTTTCGAG Hind III
C 3'-TTCGAGAGCTC Xho I

| REACTION CONDITIONS | REPAIR (fmol/20 min) | | | |
|---|---|---|---|---|
| COMPLETE | 15 (<1) | 17 (<1) | 8 (<1) | 10 (<1) |
| - Mut H | <1 | 18 | 1 | 9 |
| - Mut L | <1 | <1 | <1 | <1 |
| - Mut S | <1 | <1 | <1 | 1 |
| - SSB | 2 | <1 | <1 | <1 |
| - pol III holoenzyme | <1 | <1 | <1 | <1 |

| LIGASE | MutH | REPAIR (fmol/20 min) | | | | |
|---|---|---|---|---|---|---|
| − | − | 19 (<1) | 9 (<1) | 11 (<1) | 19 (<1) | 9 (<1) |
| + | − | 2 | <1 | 1 | 2 | 1 |
| + | + | 20 | 7 | 2 | 15 | 1 |

METHODS FOR MAPPING GENETIC MUTATIONS

This invention was made with Government support under Contract No. GM-23719 awarded by the National Institutes of Health. The Government has certain rights in the invention. This application is a continuation of application Ser. No. 08/002,529, filed Jan. 11, 1993, now abandoned, which is a continuation application Ser. No. 07/350,983, filed May 12, 1989, abandoned.

FIELD OF THE INVENTION

The present invention relates to methods for mapping genetic differences among deoxyribonucleic acid ("DNA") molecules, especially mutations involving a difference in a single base between the base sequences of two homologous DNA molecules. More specifically, this invention relates to such mapping methods which employ proteins that recognize and correct mismatched DNA base pairs in double-stranded DNA. This invention also relates to the manufacture and use of certain novel products enabled by the identification and isolation of proteins that are components of mismatched base pair recognition and correction systems.

BACKGROUND OF THE INVENTION

Mapping of genetic differences between individuals is of growing importance for both forensic and medical applications. For example, DNA "fingerprinting" methods are being applied for identification of perpetrators of crimes where even small amounts of blood or sperm are available for analysis. Biological parents can also be identified by comparing DNAs of a child and a suspected parent using such means. Further, a number of inherited pathological conditions may be diagnosed before onset of symptoms, even in utero, using methods for structural analyses of DNA. Finally, it is notable that a major international effort to physically map and, ultimately, to determine the sequence of bases in the DNA encoding the entire human genome is now underway and gaining momentum in both institutional and commercial settings.

DNA molecules are linear polymers of subunits called nucleotides. Each nucleotide comprises a common cyclic sugar molecule, which in DNA is linked by phosphate groups on opposite sides to the sugars of adjoining nucleotides, and one of several cyclic substituents called bases. The four bases commonly found in DNAs from natural sources are adenine, guanine, cytosine and thymine, hereinafter referred to as A, G, C and T, respectively. The linear sequence of these bases in the DNA of an individual encodes the genetic information that determines the heritable characteristics of that individual.

In double-stranded DNA, such as occurs in the chromosomes of all cellular organisms, the two DNA strands are entwined in a precise helical configuration with the bases projecting inward and so aligned as to allow interactions between bases from opposing strands. The two strands are held together in precise alignment mainly by hydrogen bonds which are permitted between bases by a complementarity of structures of specific pairs of bases. This structural complementarity is determined by the chemical natures and locations of substituents on each of the bases. Thus, in double-stranded DNA, normally each A on one strand pairs with a T from the opposing strand, and, likewise, each G with an opposing C.

When a cell undergoes reproduction, its DNA molecules are replicated and precise copies are passed on to its descendants. The linear base sequence of a DNA molecule is maintained in the progeny during replication in the first instance by the complementary base pairings which allow each strand of the DNA duplex to serve as a template to align free nucleotides with its polymerized nucleotides. The complementary nucleotides so aligned are biochemically polymerized into a new DNA strand with a base sequence that is entirely complementary to that of the template strand.

Occasionally, an incorrect base pairing does occur during replication, which, after further replication of the new strand, results in a double-stranded DNA offspring with a sequence containing a heritable single base difference from that of the parent DNA molecule. Such heritable changes are called genetic mutations, or more particularly in the present case, "single base pair" or "point" mutations. The consequences of a point mutation may range from negligible to lethal, depending on the location and effect of the sequence change in relation to the genetic information encoded by the DNA.

The bases A and G are of a class of compounds called purines, while T and C are pyrimidines. Whereas the normal base pairings in DNA (A with T, G with C) involve one purine and one pyrimidine, the most common single base mutations involve substitution of one purine or pyrimidine for the other (e.g., A for G or C for T), a type of mutation referred to as a "transition". Mutations in which a purine is substituted for a pyrimidine, or vice versa, are less frequently occurring and are called "transversions". Still less common are point mutations comprising the addition or loss of a single base arising in one strand of a DNA duplex at some stage of the replication process. Such mutations are called single base "insertions" or "deletions", respectively, and are also known as "frameshift" mutations, due to their effects on translation of the genetic code into proteins. Larger mutations affecting multiple base pairs also do occur and can be important in medical genetics, but their occurrences are relatively rare compared to point mutations.

Mapping of genetic mutations involves both the detection of sequence differences between DNA molecules comprising substantially identical (i.e., homologous) base sequences, and also the physical localization of those differences within some subset of the sequences in the molecules being compared. In principle, it is possible to both detect and localize limited genetic differences, including point mutations within genetic sequences of two individuals, by directly comparing the sequences of the bases in their DNA molecules. In practice, however, direct DNA sequencing has highly restricted usefulness for mapping mutations due to the major time and effort required to determine the sequence of even one DNA fragment comprising a few hundred base pairs. Typically, a single functional unit of genetic information, a gene, may be encoded in tens of thousands of base pairs of human chromosomal DNA. Thus comparing the sequence of a complete gene from one individual with that of another by direct DNA sequencing involves analyses of multiple short fragments of that gene, requiring many months if not years of effort. It may also be noted that there are estimated to be hundreds of thousands of genes in the entire human gene complement or genome, as it is called, any one of which may be involved in some genetically determined disease.

Accordingly, several simpler methods for detecting differences between DNA sequences have been developed which although providing less direct information about base sequence differences, nevertheless do yield useful observations under limited circumstances. For example, some pairs of single-stranded DNA fragments with sequences differing in a single base may be distinguished by their different migration rates in electric fields, as in denaturing gradient gel electrophoresis. This method does not detect all the possible single-base differences between DNA fragments and is restricted to fragments comprising at most a few hundred base pairs. Further, it is technically difficult to generate consistent analyses using this method. Thus this approach has extremely limited utility for detection and localization of single base sequence differences between DNAs encoding whole genes.

DNA restriction systems found in bacteria, for example, comprise proteins which generally recognize specific sequences in double-stranded DNA composed of 4 to 6 or more base pairs. In the absence of certain modifications (e.g., a covalently attached methyl group) at definite positions within the restriction recognition sequence, endonuclease components of the restriction system will cleave both strands of a DNA molecule at specific sites within or near the recognition sequence. Such short recognition sequences occur by chance in all natural DNA sequences, once in every few hundred or thousand base pairs, depending on the recognition sequence length. Thus, digestion of a DNA molecule with various restriction endonucleases, followed by analyses of the sizes of the resulting fragments (e.g., by gel electrophoresis), may be used to generate a physical map ("fingerprint") of the locations in a DNA molecule of selected short sequences.

It is well known in the art that comparisons of such restriction maps of two homologous DNA sequences can reveal differences within those specific sequences that are recognized by those restriction enzymes used in the available maps. Restriction map comparisons may localize any detectable differences within limits defined ultimately by the resolving power of DNA fragment size determination, essentially within about the length of the restriction recognition sequence under certain conditions of gel electrophoresis. To achieve such resolution in location of a point mutation by restriction mapping, however, all fragments resulting from digestion with each restriction nuclease must be within a range of distinguishable sizes, usually below an upper limit of between 10 and 20 thousand base pairs (kbp), and preferably less than one kbp, using standard gel electrophoresis techniques. Since each different restriction enzyme scans only a fraction of a percent of all the sequences in any DNA molecule, literally thousands of analyses with thousands of different enzymes would be needed to completely compare two DNAs encoding even one gene, assuming that enzymes recognizing all possible 4 to 6 base sequences were known, which they are not.

In practice, selected heritable differences in restriction fragment lengths (i.e., restriction fragment length polymorphisms, "RFLP"s) have been extremely useful, for instance, for generating physical maps of the human genome on which genetic defects may be located with a relatively low precision of hundreds or, sometimes, tens of thousands of base pairs. Typically, RFLPs are detected in human DNA isolated from small tissue or blood samples by using radioactively labeled DNA fragments complementary to the genes of interest. These "probes" are allowed to form DNA duplexes with restriction fragments of the human DNA after separation by electrophoresis, and the resulting radioactive duplex fragments are visualized by exposure to photographic (e.g., X-ray sensitive) film, thereby allowing selective detection of only the relevant gene sequences amid the myriad of others in the genomic DNA.

When the search for DNA sequence differences can be confined to specific regions of known sequence, the recently developed "polymerase chain reaction" ("PCR") technology can be used to reduce the amount of effort needed to detect and locate a single base difference as compared to the usual DNA sequencing approach which requires molecular cloning of the DNA fragment of interest. Briefly, this method utilizes short DNA fragments complementary to sequences on either side of the location to be analyzed to serve as points of initiation for DNA synthesis (i.e., "primers") by purified DNA polymerase. The resulting cyclic process of DNA synthesis results in massive biochemical amplification of the sequences selected for analysis, which then may be easily detected and, if desired, further analyzed, for example, by restriction mapping or direct DNA sequencing methods. In this way, selected regions of a human gene comprising a few kbp may be amplified and examined for sequence variations, but only in cases where sequences spanning a particular location of interest are known.

In clinical practice, the PCR method is of limited utility, for example, in detection of known heritable variants of selected human genes which differ by only one or a few specific base pairs (i.e., allelic forms a gene). For example, the human β-globin gene comprises several alleles that can be distinguished by this approach; but the overall utility is highly limited, particularly when faced with a need to detect sequence differences which may be scattered over large stretches of a gene, as in the diagnosis of conditions resulting from frequent new mutational events in human populations, in the Lesch-Nyan syndrome, for example.

Another known method for detecting and localizing single base differences within homologous DNA molecules involves the use of a radiolabeled RNA fragment with base sequence complementary to one of the DNAs and a nuclease that recognizes and cleaves single-stranded RNA. The structure of RNA is highly similar to DNA, except for a different sugar and the presence of uracil (U) in place of T; hence, RNA and DNA strands with complementary sequences can form helical duplexes ("DNA:RNA hybrids") similar to double-stranded DNA, with base pairing between A's and U's instead of A's and T's. It is known that the enzyme ribonuclease A ("RNase A") can recognize some single pairs of mismatched bases (ie., "base mispairs") in DNA:RNA hybrids and can cleave the RNA strand at the mispair site. Analysis of the sizes of the products resulting from RNase A digestion allows localization of single base mismatches, potentially to the precise sequence position, within lengths of homologous sequences determined by the limits of resolution of the RNA sizing analysis (Myers, R. M. et al., 1985, *Science*, 230, 1242–1246). RNA sizing is performed in this method by standard gel electrophoresis procedures used in DNA sequencing, an approach which limits the practical resolution to mapping of single base mispairs in a DNA:RNA hybrid comprising an RNA of only several hundred nucleotides. Moreover, this RNAse A method requires preparing complementary RNA probes from each DNA sequence to be examined, which requires more work and is more technically demanding than methods using only DNA (such as restriction mapping). Further, RNase A does not efficiently recognize all possible mispairings of DNA and RNA bases, resulting in a significant inefficiency in detection of all point differences between DNA sequences.

It has also been reported that S1 nuclease, an endonuclease specific for single-stranded nucleic acids, can recognize and cleave limited regions of mismatched base pairs in DNA:DNA or DNA:RNA duplexes. Therefore, it has been suggested that S1 nuclease could be used to map single base pair differences between DNA molecules by sizing of cleavage fragments. However, more extensive analysis of this enzyme has established that a mismatch of at least about 4 consecutive base pairs actually is generally required for recognition and cleavage of a duplex by S1 nuclease, thus precluding its use for detection of any point mutations.

Thus, none of the available methods for comparing the base sequences of DNAs, other than direct sequencing, can efficiently detect and localize all possible single base differences. Further, all of these methods, including especially DNA sequencing, require substantial labor and repetitive analyses with various sequence specific reagents (e.g., multiple nucleases or short nucleic acid strands) to detect all single base differences within two specimens of a single human gene.

Hence, there is a need for simpler and more efficient approaches, both for detecting and for localizing genetic differences between DNA sequences to facilitate both clinical diagnoses and forensic investigations. In particular, the observations above indicate a specific need for simpler and more efficient methods and reagents for detection of any possible single base differences between long DNA sequences, for example, between a complete gene from one individual and the entire genome of another. There is also a further need for simpler methods for localization of any possible single base differences within the sequences of homologous regions of long DNA molecules such as those encoding one or more complete genes and comprising several kbp of DNA.

The present invention contemplates the use of certain proteins that recognize mismatched base pairs in double-stranded DNA (and, therefore, are called "mispair recognition proteins") in defined systems for detecting and mapping point mutations in DNAs. Accordingly, it is an object of the present invention to provide methods for using such mispair recognition proteins, alone or in combination with other proteins, for detecting and localizing single base differences between DNA molecules, particularly those DNAs comprising several kbp. Additionally, it is an object of this invention to develop modified forms of mispair recognition proteins to further simplify methods for identifying specific bases which differ between DNAs.

Enzymatic systems capable of recognition and correction of base pairing errors within the DNA helix have been demonstrated in bacteria, fungi and mammalian cells, but the mechanisms and functions of mismatch correction are best understood in *Escherichia coli*. Of the several mismatch repair systems that have been identified in *E. coli*, the most relevant here is the methyl-directed pathway for repair of DNA biosynthetic errors. The fidelity of DNA replication in *E. coli* is enhanced 100–1000 fold by this postreplication mismatch correction system. This system processes base pairing errors within the helix in a strand-specific manner by exploiting patterns of DNA methylation. Since DNA methylation is a postsynthetic modification, newly synthesized strands temporarily exist in an unmethylated state, with the transient absence of adenine methylation on GATC sequences directing mismatch correction to new DNA strands within the hemimethylated duplexes.

In vivo analyses in *E. coli* have shown that selected examples of each of the different mismatches are subject to correction with different efficiencies. G-T, A-C, G-G and A-A mismatches are typically subject to efficient repair. A-G, C-T, T-T and C-C are weaker substrates, but well repaired exceptions exist within this class. It is thought that the sequence environment of a mismatched base pair may be an important factor in determining the efficiency of repair in vivo. The mismatch correction system is also capable in vivo of correcting differences between duplexed strands involving a single base insertion or deletion. Further, genetic analyses have demonstrated that the mismatch correction process requires intact genes for several proteins, including the products of the mutH, mutL and mutS genes, as well as DNA helicase II and single-stranded DNA binding protein (SSB).

The present inventors have been seeking to identify and isolate specific proteins that are required for correction of mismatched base pairs and to understand the specific biochemical functions of these mispair correction system components. The products of the mutH and mutS genes have been purified to near homogeneity in biologically active form. Analysis of the MutH protein has suggested that it functions in strand discrimination by incising the unmethylated DNA strand at GATC sites. The isolated MutS protein has been shown to recognize four of the eight possible mismatched base pairs (specifically, G-T, A-C, A-G and C-T mispairs; Su, S. -S. and Modrich, P., 1986, *Proc. Nat. Acad. Sci. U.S.A.*, 84, 5057–5061). The hierarchy of apparent affinities of isolated MutS protein for the particular examples of the four mispairs tested in these studies did not correlate well with in vivo efficiencies of mismatch correction. Hence, these studies left undetermined whether or not additional proteins, acting alone or in concert with MutS, are required for or influence the recognition of other base mispairs.

SUMMARY OF THE INVENTION

It has now been discovered that a single DNA base mispair recognition protein can form specific complexes with any of the eight possible mismatched base pairs embedded in an otherwise homologous DNA duplex. It has also been revealed that another mispair recognition protein can recognize only one specific base pair mismatch, A-G, and in so doing, it chemically modifies a nucleotide at the site of the mispair. In addition, defined in vitro systems have been established for carrying out methyl-directed mismatch repair processes. Accordingly, the present invention contemplates the use of such mispair recognition proteins and related correction system components to detect and to localize point mutations in DNAs.

For clarity in the following discussion, it will be useful to point out here certain distinctions related to the fact that some proteins that recognize DNA base mispairs are merely DNA binding proteins, while others modify the DNA as a consequence of mispair recognition. Notwithstanding the fact that in the latter situation the protein modifying the DNA may be associated with the DNA only transiently, hereinafter, whether a mispair recognition protein is capable of DNA binding only or also of modifying DNA, whenever it is said that a protein recognizes a DNA mispair, this is equivalent to saying that it "forms specific complexes with" or "binds specifically to" that DNA mispair in double-stranded DNA. In the absence of express reference to modification of DNA, reference to DNA mispair recognition does not imply consequent modification of the DNA. Further, the phrase "directs modification of DNA" includes both cases wherein a DNA mispair recognition protein has an inherent DNA modification function (e.g., a glycosylase) and cases wherein the mispair recognition protein merely forms specific complexes with mispairs, which complexes are then recognized by other proteins that modify the DNA in the vicinity of the complex. Finally, it should be noted in the following discussion that those DNA base mispairs (e.g., A-G or C-C) which are recognized by a given protein are referred to as the "cognate" base mispairs for that protein.

Accordingly, the present invention relates to a method for detecting base sequence differences within homologous regions of two DNA molecules comprising the steps of contacting at least one strand of the first DNA molecule with the complementary strand of the second DNA molecule under conditions such that base pairing occurs, contacting the resulting DNA duplexes with a protein that recognizes substantially all base pair mismatches under conditions such that the protein forms specific complexes with its cognate mispairs, and detecting the resulting DNA:protein complexes by a suitable analytical method.

In the practice of a preferred embodiment of this aspect of this invention, the mispair recognition protein is the product of the mutS gene of E. coli or another functionally homologous protein, and an advantageous analytical method for detecting the DNA:protein complex comprises the steps of contacting the DNA:protein complexes with a selectively adsorbent agent, such as a membranous nitrocellulose filter, under conditions such that protein:DNA complexes are retained on the agent while DNA not complexed with protein is not retained, and measuring the amount of DNA in the retained complexes. Other suitable analytical methods for detecting the DNA:protein complex are disclosed.

In addition to methods designed merely to detect base sequence differences between DNAs, this invention further relates to a method for both detecting and localizing individual base sequence differences within homologous regions of two DNA molecules comprising the steps of contacting at least one strand of the first DNA molecule with the complementary strand of the second DNA molecule under conditions such that base pairing occurs, contacting the resulting double-stranded DNA duplexes with a protein that recognizes at least one base mispair under conditions such that the protein forms specific complexes with its cognate mispairs and thereby directs modification of at least one strand of the DNA in the resulting DNA:protein complexes in the vicinity of the DNA:protein complex, and determination of the location of the resulting DNA modification relative to a known sequence within the homologous regions of the DNAs by a suitable analytical method.

In the practice of one embodiment of this aspect of this invention, the mispair recognition protein is the product of the mutS gene of E. coli or is another functionally homologous protein; the step in which the DNA is modified in the vicinity of the DNA:protein complex further comprises contacting the DNA:MutS protein complex with a defined E. coli DNA mismatch correction system under conditions such that single-stranded gaps are produced in the vicinity of the complexed protein; and the method for determining the locations of these single-stranded gaps within the DNA duplex comprises the steps of cleaving the DNA with a single-strand specific endonuclease and at least one restriction endonuclease, and comparing the electrophoretic mobilities of the resulting modified DNA fragments with DNA restriction fragments not contacted with the defined mismatch correction system. Suitable single-strand specific endonucleases include the S1 single-strand specific nuclease, for example, or other functionally similar nucleases well known in the art.

The present invention further relates, in part, to forms of mispair recognition proteins which have been altered to provide an inherent means for modifying at least one strand of the DNA duplex in the vicinity of the bound mispair recognition protein.

In a principal embodiment of this aspect of this invention, the altered mispair recognition protein is the modified product of the mutS gene of E. coli or is another functionally homologous modified protein to which is attached an hydroxyl radical cleaving function; and the DNA modification step in the DNA mispair localization method further comprises contacting this modified protein with the DNA in under conditions such that the radical cleaving function cleaves at least one strand of the DNA in the vicinity of the protein. Additional altered forms of mispair recognition proteins that modify at least one strand of the DNA in a DNA:protein complex in the vicinity of the bound protein are disclosed.

The present invention also comprises another E. coli DNA mispair recognition protein that recognizes only A-G mispairs without any apparent requirement for hemimethylation. This protein, the product of the mutY gene, is a glycosylase which specifically removes the adenine from an A-G mispair in a DNA duplex. Accordingly, this MutY protein is useful for the specific detection of A-G mispairs according to the practice of the present invention.

DESCRIPTION OF SPECIFIC EMBODIMENTS

Figure 1:
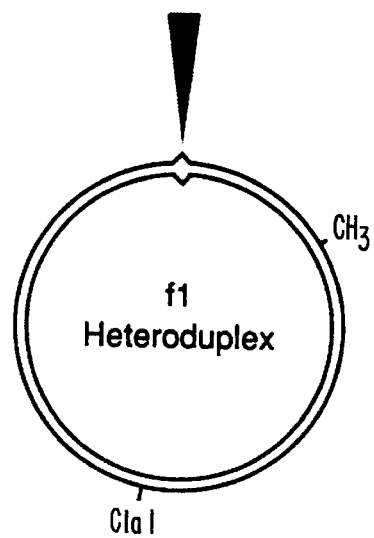
FIG. 1. Heteroduplex substrate for in vitro mismatch correction. Each substrate used in this study is a 6440-bp, covalently closed, circular heteroduplex that is derived from bacteriophage f1 and contains a single base-base mismatch located within overlapping recognition sites for two restriction endonucleases at position 5632. In the example shown a G-T mismatch resides within overlapping sequences recognized by Hind III and Xho I endonucleases. Although the presence of the mispair renders this site resistant to cleavage by either endonuclease, repair occurring on the complementary (c) DNA strand yields an A-T base pair and generates a Hind III-sensitive site, while correction on the viral (v) strand results in a G-C pair and Xho I-sensitivity. The heteroduplexes also contain a single d(GATC) sequence 1024 base pairs from the mismatch (shorter path) at position 216. The state of strand methylation at this site can be controlled, thus permitting evaluation of the effect of DNA methylation on the strand specificity of correction.

The present invention relates to a method for detecting base sequence differences within homologous regions of two DNA molecules comprising the steps of contacting at least one strand of the first DNA molecule with the complementary strand of the second DNA molecule under conditions such that base pairing occurs, contacting the resulting DNA duplexes with a protein that recognizes at least one base pair mismatch under conditions such that the protein forms specific complexes with its cognate mispairs, and detecting the resulting DNA:protein complexes by a suitable analytical method.

In the practice of this method, the two DNA molecules to be compared may comprise natural or synthetic sequences encoding up to the entire genome of an organism, including man, which can be prepared by well known procedures. Detection of bases sequence differences according to this method of this invention does not require cleavage (by a restriction nuclease, for example) of either of the two DNAs, although it is well known in the art that rate of base pair formation between complementary single-stranded DNA fragments is inversely related to their size. This detection method requires that base sequence differences to be detected lie within a region of homology constituting at least about 14 consecutive base pairs of homology between the two DNA molecules, which is about the minimum number of base pairs generally required to form a stable DNA duplex. Either one or both of the strands of the first DNA may be selected for examination, while at least one strand of the second DNA complementary to a selected first DNA strand must be used. The DNA strands, particularly those of the second DNA, advantageously may be radioactively labeled to facilitate direct detection, according to procedures well known in the art.

Methods and conditions for contacting the DNA strands of the two DNAs under conditions such that base pairing occurs are also widely known in the art.

In the practice of a principal embodiment of this aspect of this invention, the mispair recognition protein is the product of the mutS gene of E. coli. Preparation of this protein substantially free of other proteins has been reported previously (Su, S. -S. and Modrich, P., 1986, Proc. Nat. Acad. Sci. U.S.A., 84, 5057–5061, which is hereby incorporated herein by reference).

The surprising ability of the MutS protein to recognize examples of all eight single base pair mismatches within double-stranded DNA, even including C-C mispairs which do not appear to be corrected in vivo, is demonstrated by the fact that MutS protein protects DNA regions containing each mismatch from hydrolysis by DNase I (i.e., by "DNase I footprint" analyses), as recently reported (Su, S. -S., et al., 1988, J. Biol. Chem., 263, 6829–6835). The affinity of MutS protein for the different mispairs that have been tested varies considerably. Local sequence environment may also affect the affinity of the MutS protein for any given base mispair; in other words, for example, the affinity for two specific cases of A-C mispairs, which are surrounded by different sequences, may not be the same. Nevertheless, no examples of base mispairs have been found that are not recognized by isolated MutS protein. Accordingly, it is believed that this method of this invention detects substantially all possible single base differences between homologous regions of any two DNA molecules.

It should be particularly noted that the DNA duplexes which MutS recognizes are not required to contain GATC sequences and, hence, they do not require hemimethylation of A's in GATC sequences, the specific signal for the full process of mispair correction in vivo; therefore, use of MutS in this method allows recognition of a DNA base mispair in DNAs lacking such methylation, for instance, DNAs isolated from human tissues.

A protein which appears to be functionally and in part, at least, structurally homologous to the *E. coli* MutS protein has also been discovered in a methyl-directed mispair correction system in *Salmonella typhimurium* bacteria (Pang et al., 1985, *J. Bacteriol.,* 163, 1007–1015). The gene for this protein has been shown to complement *E. coli* strains with mutations inactivating the mutS gene and the amino acid sequence of its product shows homology with that of the *E. coli* MutS protein. Accordingly, this *S. typhimurium* protein is also believed to be suitable for the practice of this aspect of the present invention. Other organisms, including man, are known to possess various systems for recognition and repair of DNA mispairs, which, as one skilled in the art would appreciate, comprise mispair recognition proteins functionally homologous to the MutS protein. Accordingly, it is believed that such DNA base mispair recognition proteins are also suitable for use in the present invention.

In the practice of a preferred embodiment of this aspect of this invention, an advantageous analytical method for detecting the DNA:protein complex comprises the steps of contacting the DNA:protein complexes with a selectively adsorbent agent, such as a membranous nitrocellulose filter, under conditions such that protein:DNA complexes are retained on the agent while DNA not complexed with protein is not retained, and measuring the amount of DNA in the retained complexes. Absent radioactive labeling of at least one strand used to form the DNA duplexes, the DNA in complexes on the filter may be detected by any of the usual means in the art for detection of DNA on a solid substrate, including annealing with complementary strands of radioactive DNA.

The nitrocellulose filter method for detecting complexes of MutS protein with base mispairs in DNA has been reported in detail (Jiricny, J. et al., 1988, *Nuc. Acids Res.* 16, 7843–7853, which is hereby incorporated herein by reference). Besides simplicity, a major advantage of this method for detecting the DNA:protein complex over other suitable methods is the practical lack of a limitation on the size of DNA molecules that can be detected in DNA:protein duplexes. Therefore, this embodiment of this method is useful for detecting single base sequence differences between DNA fragments as large as can be practically handled without shearing, at least 50 kbp.

Another suitable analytical method for detecting the DNA:protein complex between the mispair recognition protein and a cognate mispair in a DNA duplex comprises the steps of separating the DNA:protein complexes from DNA that does not form such complexes on the basis of electrophoretic mobility, and detecting the DNA in the less mobile DNA:protein complexes. The DNA in the DNA:protein complexes may be detected by any of the usual standard means for detection of DNA in gel electrophoresis, including staining with dyes or annealing with complementary strands of radioactive DNA. Detecting complexes comprising the MutS base mispair recognition protein and mispairs in DNA duplexes is also described in the foregoing reference (Jiricny, J. et al., 1988, *Nuc. Acids Res.,* 16, 7843–7853). Under the usual conditions employed in the art for detecting specific DNA:protein complexes by gel electrophoresis, complex formation of a protein with a double-stranded DNA fragment of up to several hundred base pairs is known to produce distinguishable mobility differences.

Other suitable analytical methods for detecting the DNA:MutS protein complex include immunodetection methods using an antibody specific for the base mispair recognition protein. For example, antibodies specific for the *E. coli* MutS protein have been prepared readily by standard immunological techniques. Accordingly, one immunodetection method for complexes of MutS protein with DNA comprises the steps of separating the DNA:protein complexes from DNA that does not form such complexes by immunoprecipitation with an antibody specific for MutS protein, and detecting the DNA in the precipitate. According to the practice of this aspect of this invention, quantitative immunoassay methods known in the art may be employed to determine the number of single base mispairs in homologous regions of two DNA molecules, based upon calibration curves that can be established using complexes of a given mispair recognition protein with DNA duplexes having known numbers of mispairs.

In addition to methods that merely detect base sequence differences, this invention further relates to a method for both detecting and localizing individual base sequence differences within homologous regions of two DNA molecules comprising the steps of contacting at least one strand of the first DNA molecule with the complementary strand of the second DNA molecule under conditions such that base pairing occurs, contacting the resulting double-stranded DNA duplexes with a protein that recognizes at least one base mispair under conditions such that the protein forms specific complexes with its cognate mispairs and thereby directs modification of at least one strand of the DNA in the resulting DNA:protein complexes in the vicinity of the DNA:protein complex, and determination of the location of the resulting DNA modification relative to a known sequence within the homologous regions of the DNAs by a suitable analytical method.

In the method of the present invention for localization of single base differences, there is provided a suitable means for modifying at least one strand of the DNA duplex in the vicinity of the bound mispair recognition protein. The modification may be any alteration for which there is a means of detection, for instance a chemical modification including breaking of a chemical bond resulting in, as examples, cleavage between nucleotides of at least one DNA strand or removal of a base from the sugar residue of a nucleotide. Specific means for modifying DNAs in the vicinity of the DNA:protein complex are provided below for several embodiments of this aspect of the invention, together with interpretations of the phrase "in the vicinity of", as appropriate to the practical limitations of the modification approach in each instance.

In the practice of one embodiment of this aspect of this invention, the mispair recognition protein is the product of the mutS gene of *E. coli* or is another functionally homologous protein; and the step in which the DNA is modified in the vicinity of the DNA:protein complex further comprises contacting the DNA:MutS protein complex with a defined *E. coli* DNA mismatch correction system under conditions such that single-stranded gaps are produced in the vicinity of the complexed protein.

The complete defined mismatch correction system comprises the following purified components: *E. coli* MutH, MutL, and MutS proteins, DNA helicase II, single-strand DNA binding protein, DNA polymerase III holoenzyme, exonuclease I, DNA ligase, ATP, and the four deoxynucleoside triphosphates. This set of proteins can process seven of the eight base-base mismatches in a strand-specific reaction that is directed by the state of methylation of a single GATC sequence located 1 kilobase from the mispair. This defined system is described further in Example 1, below. It should be noted that the lack of ability to repair C-C base mispairs in this embodiment of this aspect of the present invention is not a major limitation of the method for detecting all possible base sequence differences between any two naturally occurring DNA sequences because mutations apparently due to C-C mispairing during DNA replication appear arise most infrequently in vivo.

For the purposes of generating single-stranded gaps in the vicinity of the DNA:MutS protein complexes, DNA duplexes containing mispaired base pairs are contacted with the defined mismatch correction system under the standard conditions described in Example 1, Table 3 (Complete reaction), except for the following differences: exogenous dNTP's are omitted or, preferably, 2',3'-dideoxynucleoside-5'-triphosphates (ddNTPs) are added at 100 uM with dNTPs at 10 uM, to inhibit repair of single-strand gaps; and DNA ligase may be omitted from the reaction. The requirement for methyl-directed strand incision by MutH may be obviated by provision of a single-stand nick by some other means within the vicinity of the mispair, as described in Example 1, FIG. 5. A suitable means for inducing such nicks in unmethylated DNA is limited contact with a nuclease, DNase I, for example; under conditions that are well known in the art, this approach creates nicks randomly throughout double-stranded DNA molecules at suitable intervals for allowing the mispair correction system to create single-stranded gaps in the vicinity of a mispair anywhere in the DNA.

It should be noted that in this embodiment of this method for localizing mismatch base pairs, "in the vicinity of" a base mispair is defined practically by the size of the single-strand gaps typically observed under the above conditions, namely up to about one kbp from the mismatch base pair. Further, in this embodiment, the method for determining the locations of these single-stranded gaps within the DNA duplex comprises the steps of cleaving the DNA with a single-strand specific endonuclease and at least one restriction endonuclease, and comparing the electrophoretic mobilities of the resulting modified DNA fragments with DNA restriction fragments not contacted with the defined mismatch correction system. Suitable single-strand specific endonucleases include the S1 single-strand specific nuclease, for example, or other functionally similar nucleases well known in the art. Additional restriction mapping may be performed as needed to further localize any fragment modifications observed in initial applications of the method, until, if desired, a restriction fragment of convenient size for direct sequence determination is obtained for direct comparisons of sequences of the two DNA molecules in the vicinity of the base sequence difference.

The present invention further relates, in part, to forms of mispair recognition proteins which have been altered to provide an inherent means for modifying at least one strand of the DNA duplex in the vicinity of the bound mispair recognition protein.

In a principal embodiment of this aspect of this invention, the altered mispair recognition protein is the modified product of the mutS gene of E. coli or is another functionally homologous modified protein to which is attached an hydroxyl radical cleaving function; and the DNA modification step in the DNA mispair localization method further comprises contacting this modified protein with the DNA under conditions such that the radical cleaving function cleaves at least one strand of the DNA in the vicinity of the protein.

Several methods for attaching an hydroxyl radical cleaving function to a DNA binding protein are known in the art. For example, lysyl residues may be modified by chemically attaching the 1,10-phenanthroline-copper complex to lysine residues, resulting in conversion of a DNA binding protein into a highly efficient site-specific nuclease that cleaved both DNA strands (in the presence of hydrogen peroxide as a coreactant) within the 20 base pair binding site of the protein, as determined by DNase I footprinting (C. -H. Chen and D. S. Sigman, 1987, Science, 237, 1197). Chemical attachment of an EDTA-iron complex to the amino terminus of another DNA binding protein similarly produced a sequence specific DNA cleaving protein that cut both strands of the target DNA within a few bases of recognition site of similar size (J. P. Sluka, et al., 1987, Science, 235, 777).

An alternate means for attaching the hyroxyl radical cleaving function to this same protein involved extension of the amino terminus with the three amino acids, Gly-Gly-His, which is consensus sequence for the copper-binding domain of serum albumin (D. P. Mack et al., 1988, J. Am. Chem. Soc., 110, 7572–7574). This approach allows for preparation of such an artificial DNA cleaving protein directly by recombinant methods, or by direct synthesis using standard solid phase methods, when the peptide is sufficiently short as it was in this case (55 residues including the 3 added amino acids), thereby avoiding the need for an additional chemical modification step of the reagent which is both time consuming and difficult in large scale production. In contrast to the EDTA-iron complex, the particular peptide sequence constructed in this instance cleaved only one example out of four recognition sites in different sequence environments.

Nevertheless, one skilled in the art of protein engineering would appreciate that this general approach for converting a DNA binding protein into a DNA cleaving protein by attachment of an hydrogen radical cleavage function is widely applicable. Hence, DNA base mispair recognition proteins which normally only bind to DNA are modified to cleave DNA by attachment of an hydroxyl radical cleavage function, according to the practice of this aspect of this invention, without undue experimentation, by adjustment of appropriate variables taught in the art, particularly the chemical nature and length of the "spacer" between the protein and the metal binding site.

In the DNA sequence localization method according to this embodiment which employs a modified DNA base mispair recognition protein with attached hydroxyl radical cleavage function, the means for modification of the DNA:protein complex is a suitable metal ion and associated cofactor or cofactors, and the modification comprises double-stranded cleavage of the DNA within the vicinity of any cognate base mispair wherein the "vicinity" substantially corresponds to the sequence of DNA protected by the binding of the protein to a base mispair, generally within about 20 base pairs. A single-strand specific nuclease, S1, for instance, may be used to augment cleavage by the modified base mispair recognition protein in the event that a single-strand bias is suspected in the cleavage of any DNAs with which the protein forms a specific complex.

Additional altered forms of mispair recognition proteins that modify at least one strand of the DNA in a DNA:protein complex in the vicinity of the bound protein according to the present invention include proteins comprising the portions or "domains" of the unmodified base mispair recognition enzymes that are essential for binding to a DNA mispair. These essential domains comprise peptides in the unmodified protein which are made resistant to proteolytic digestion by formation of specific DNA:protein complexes at cognate DNA base mispairs. These essential DNA binding domains further comprise peptide sequences that are most highly conserved during evolution; such conserved domains are evident, for example, in comparisons of the sequences of the *E. coli* MutS protein with functionally homologous proteins in *S. typhimurium* and other structurally similar proteins. Accordingly, peptide sequences of a DNA base mispair recognition protein that are protected from proteases by formation of specific complexes with mispairs in DNA and, in addition or in the alternative, are evolutionarily conserved, form the basis for a particularly preferred embodiment of this aspect of the present invention, since such peptides constitute less than half the mass of the intact protein and, therefore, are advantageous for production and, if necessary, for chemical modification to attach a cleavage function for conversion of the DNA binding protein into a DNA cleavage protein specific for sites of DNA base mispairs.

The present invention also comprises another *E. coli* DNA mispair recognition protein that recognizes only A-G mispairs without any requirement for hemimethylation. This protein, the product of the mutY gene, is a glycosylase which specifically removes the adenine from an A-G mispair in a DNA duplex. The Mut Y protein has been purified to near homogeneity by virtue of its ability to restore A-G to C-G mismatch correction to cell-free extracts (K. G. Au et al., *Proc. Nat. Acad. Sci. U.S.A.*, 85, 9163, 1988) of a mutS mutY double mutant strain of *E. coli*, as described in Example 2, below. It is a 36 kDa polypeptide that apparently exists as a monomer in solution. MutY, an AP endonuclease, DNA polymerase I, and DNA ligase are sufficient to reconstitute MutY-dependent, A-G to C-G repair in vitro. A DNA strand that has been depurinated thusly by the MutY protein is susceptible to cleavage by any of several types of AP (apurinic) endonuclease (e.g., human AP endonuclease II) or by piperidine, under conditions that are well known in the art. The cleavage products are then analyzed by gel electrophoresis as in DNA sequencing. Accordingly, this MutY protein is useful in a method for the specific detection and localization of A-G mispairs, according to the practice of the present invention.

The full novelty and utility of the present invention may be further appreciated by reference to the following brief description of selected specific embodiments which advantageously employ various preferred forms of the invention as applied to a common problem in genetic mapping of point mutations in the human genome. In the course of constructing gene linkage maps, for example, it is frequently desirable to compare the sequence of a DNA cloned fragment comprising twenty or more kbp of unknown sequence (except, perhaps, for a few restriction enzyme recognition sites) with homologous sequences in DNA extracted from a human tissue sample. While fragments containing sequences homologous to the cloned DNA fragment can be detected in the human tissue DNA by the well known "Southern" blotting method using radiolabeled DNA of the clone, as explained in the Background section, detection and localization of all the sequence differences between such a clone and a human DNA sample would be a long and arduous task at best using the best methods available in the prior art, including restriction enzyme mapping and direct DNA sequencing.

In contrast, substantially all base pairs in the entire homologous sequence of the cloned DNA fragment are compared to those of the human tissue DNA, most advantageously in a single test according to the present invention, merely by contacting both strands of the human tissue DNA molecule with both radiolabeled complementary strands of the second DNA molecule (usually without separation from the cloning vector DNA) under conditions such that base pairing occurs, contacting the resulting DNA duplexes with the *E. coli* MutS protein that recognizes substantially all base pair mismatches under conditions such that the protein forms specific complexes with its cognate mispairs, and detecting the resulting DNA:protein complexes by contacting the complexes with a membranous nitrocellulose filter under conditions such that protein:DNA complexes are retained while DNA not complexed with protein is not retained, and measuring the amount of DNA in the retained complexes by standard radiological methods.

If the above detection test indicates the presence of sequence differences between the human tissue DNA and the cloned DNA and localization is required, or, in the alternative, if such differences are suspected and localization as well as detection of them is desired in a first analysis, the another method of this invention may be applied for these purposes. An embodiment of this aspect of the invention that may be most advantageously employed comprises the steps of contacting both strands of the human tissue DNA molecule with both radiolabeled complementary strands of the second DNA molecule (usually without separation from the cloning vector DNA) under conditions such that base pairing occurs, contacting the resulting DNA duplexes with a modified form of MutS protein of *E. coli* to which is attached an hydroxyl radical cleaving function under conditions such that the radical cleaving function cleaves both strands of the DNA within about 20 base pairs of substantially all DNA base mispairs. In the absence of any DNA base mispairs in the DNA duplexes comprising complementary strands of the human tissue and cloned DNAs, no DNA fragments smaller than the cloned DNA (plus vector DNA, if still attached) would be detected. Determination of the location of any double-stranded DNA cleavages by the modified MutS protein to within a few kbp or less of some restriction enzyme cleavage site within the cloned DNA is determined by standard restriction enzyme mapping approaches. If greater precision in localization and identification of a single base difference is desired, sequencing could be confined to those particular fragments of cloned DNA that span at least one base sequence difference localized by this method and are cleaved by a restriction enzyme at the most convenient distance of those sequence differences for direct sequencing.

The following Examples are provided for further illustrating various aspects and embodiments of the present invention and are in no way intended to be limiting of the scope.

EXAMPLE 1

DNA Mismatch Correction in a Defined System

In order to address the biochemistry of methyl-directed mismatch correction, the reaction has been assayed in vitro using the type of substrate illustrated in FIG. 1. Application of this method to cell-free extracts of *E. coli* (A. -L. Lu, S. Clark, P. Modrich, *Proc. Natl. Acad. Sci. USA* 80, 4639, 1983) confirmed in vivo findings that methyl-directed repair requires the products of four mutator genes, mutH, mutL, mutS and uvrD (also called mutU), and also demonstrated a requirement for the E. coli single-strand DNA binding protein (SSB). The dependence of in vitro correction on mutH, mutL, and mutS gene products has permitted isolation of these proteins in near homogeneous, biologically active forms. The 97-kD MutS protein binds to mismatched DNA base pairs; the 70-kD MutL protein binds to the MutS-Heteroduplex complex (M. Grilley, K. M. Welsh, S. -S. Su, P. Modrich, *J. Biol. Chem.* 264, 1000, 1989); and the 25-kD MutH protein possesses a latent endonuclease that incises the unmethylated strand of a hemimethylated d(GATC) site (K. M. Welsh, A. -L. Lu, S. Clark, P. Modrich, *J. Biol. Chem.* 262, 15624, 1987), with activation of this activity depending on interaction of MutS and MutL with a heteroduplex in the presence of ATP (P. Modrich, *J. Biol. Chem.* 264, 6597, 1989). However, these three Mut proteins together with SSB and the DNA helicase II product of the uvrD (mutU) gene (I. D. Hickson, H. M. Arthur, D. Bramhill, P. T. Emmerson, *Mol. Gen. Genet.* 190, 265, 1983) are not sufficient to mediate methyl-directed repair. Below is described identification of the remaining required components and reconstitution of the reaction in a defined system.

Protein and cofactor requirements for mismatch correction. Methyl-directed mismatch correction occurs by an excision repair reaction in which as much as several kilobases of the unmethylated DNA strand is excised and resynthesized (A. -L. Lu, K. Welsh, S. Clark, S. -S. Su, P. Modrich, *Cold Spring Harbor Symp. Quant. Biol.* 49, 589, 1984). DNA polymerase I, an enzyme that functions in a number of DNA repair pathways, does not contribute in a major way to methyl-directed correction since extracts from a polA deletion strain exhibit normal levels of activity. However extracts derived from a dnaZ$^{ts}$ strain are temperature sensitive for methyl-directed repair in vitro (Table 1).

TABLE 1

Requirement for τ and γ Subunits of
DNA Polymerase III Holoenzyme in Mismatch Repair

| Extract genotype | DNA Pol III addition (ng) | Mismatch Correction (fmol/h/mg) Extract preincubation 42° | 34° | Activity ratio 42°/34° |
|---|---|---|---|---|
| dnaZ$^{ts}$ | — | 8 | 91 | 0.09 |
| | 57 ng | 75 | 160 | 0.47 |
| dnaZ$^+$ | — | 150 | 160 | 0.94 |
| | 57 ng | 160 | 160 | 1.0 |

Extracts from strains AX727 (lac thi str$^R$ dnaZ20-16) and AX729 (as AX727 except purE dnaz$^+$) were prepared as described (A. -L. Lu, S. Clark, P. Modrich, Proc. Natl. Acad. Sci. USA 80, 4639, 1983). Samples (110 μg of protein) were mixed with 0.8 μl of 1M KCl and water to yield a volume of 7.2 μl, and preincubated at 42° or 34° C. for 2.5 minutes. All heated samples were then placed at 34° C. and supplemented with 2.2 μl of a solution containi ng 0.1 μg (24 fmol) of hemimethylated G-T heteroduplex DNA, 16 ng of MutL protein, 50 ng of MutS protein, and buffer and nucleotide components of the mismatch correction assay (A. -L. Lu, S. Clark, P. Modrich, Proc. Natl. Acad. Sci. USA 80, 4639, 1983). DNA polymerase III holoenzyme (57 ng in 0.6 μl) or enzyme buffer was then added, and incubation at 34° C. was continued for 60 min. Heated extracts were supplemented with purified MutL and MutS proteins because these components a re labile at 42° C. Activity measurements reflect the correction of heteroduplex sites.

The dnaZ gene encodes the T and y subunits of DNA polymerase III holoenzyme (M. Kodaira, S. B. Biswas, A. Kornberg, *Mol. Gen. Genet.* 192, 80, 1983; D. A. Mullin, C. L. Woldringh, J. M. Henson, J. R. Walker, *Mol. Gen. Genet.* 192, 73, 1983), and mismatch correction activity is largely restored to heated extracts of the temperature-sensitive mutant strain by addition of purified polymerase III holoenzyme. Since DNA polymerase III holoenzyme is highly processive, incorporating thousands of nucleotides per DNA binding event, the involvement of this activity is consistent with the large repair tracts associated with the methyl-directed reaction.

Additional data indicate that purified MutH, MutL, and MutS proteins, DNA helicase II, SSB, and DNA polymerase III holoenzyme support methyl-directed mismatch correction, but this reaction is inhibited by DNA ligase, an enzyme that is shown below to be required to restore covalent continuity to the repaired strand. This observation led to isolation of a 55-kD stimulatory protein that obviates ligase inhibition. The molecular weight and N-terminal sequence of this protein indicated identity to exonuclease I (G. J. Phillips and S. R. Kushner, *J. Biol. Chem.* 262, 455, 1987), and homogeneous exonuclease I readily substitutes for the 55-kD stimulatory activity (Table 2). Thus, exonuclease I and the six activities mentioned above mediate efficient methyl-directed mismatch correction in the presence of ligase to yield product molecules in which both DNA strands are covalently continuous.

TABLE 2

Stimulation of in vitro Methyl-
Directed Correction by Exonuclease I.

| Protein added | Mismatch correction (fmol/20 min) |
|---|---|
| None | 1 |
| 55-kD protein | 18 |
| Exonuclease I | 18 |

Reactions (10 μl) contained 0.05M HEPES (potassium salt, pH 8.0), 0.02M KCl, 6 mM MgCl$_2$, bovine serum albumin (0.05 mg/ml), 1 mM dithiothreitol, 2 mM ATP, 100 μM (each) dATP, dCTP, dGTP, and dTTP, 25 μM β-AND$^+$, 0.1 μg of hemimethylated, covalently closed G-T heteroduplex DNA (FIG. 1, methylation on c strand, 24 fmol), 0.26 ng of MutH (K. M. Welsh, A. -L. Lu, S. Clark, P. Modrich, J. Biol. Chem. 262, 15624, 1987), 17 ng of MutL (M. Grilley, K. M. Welsh, S. -S. Su, P. Modrich, J. Biol. Chem. 264, 1000, 1989), 35 ng of MutS (S. -S. Su and P. Modrich, Proc. Natl. Acad. Sci. USA 83, 5057, 1986), 200 ng of SSB (T. M. Lohman, J. M. Green, R. S. Beyer, Biochemistry 25, 21, 1986; U.S. Biochemical Corp.), 10 ng of DNA helicase II (K. Kumura and M. Sekiguchi, J. Biol. Chem. 259, 1560, 1984), 20 ng of E. coli DNA ligase (U.S. Biochemical Corp.), 95 ng of DNA polymerase III holoenzyme (C. McHenry and A. Kornberg, J. Biol. Chem. 252, 6478, 1977), a nd 1 ng of 55-kD protein or exonuclease I (U.S. Biochemical Corp.) as indicated. Reactions were incubated at 37° C. for 20 minutes, quenched at 55° C. for 10 minutes, chilled on ice, and then digested with Xho I or Hind III endonuclease to monitor correction. Repair of the G-T mismatch yielded a only the G-C containing, Xho I-sensitive product.

The requirements for repair of a covalently closed G-T heteroduplex (FIG. 1) are summarized in Table 3 (Closed circular). No detectable repair was observed in the absence of MutH, MutL, or MutS proteins or in the absence of DNA polymerase III holoenzyme, and omission of SSB or exonuclease I reduced activity by 85 to 90 per cent.

TABLE 3

Protein and Cofactor Requirements for
Mismatch Correction in a Defined System.

| | Mismatch correction (fmol/20 min) | |
|---|---|---|
| Reaction conditions | Closed Circular Heteroduplex | Open Circular Heteroduplex |
| Complete | 15 | 17 (No MutH, No ligase) |
| minus MutH | <1 | — |
| minus MutL | <1 | <1 |
| minus MutS | <1 | <1 |
| minus DNA polymerase III holoenzyme | <1 | <1 |

TABLE 3-continued

Protein and Cofactor Requirements for
Mismatch Correction in a Defined System.

|  | Mismatch correction (fmol/20 min) | |
|---|---|---|
| Reaction conditions | Closed Circular Heteroduplex | Open Circular Heteroduplex |
| minus SSB | 2 | 1.4 |
| minus exonuclease I | 2 | <1 |
| minus DNA helicase II | 16 | 15 |
| minus helicase II, plus immune serum | <1 | <1 |
| minus helicase II, plus pre-immune serum | 14 | NT |
| minus Ligase/AND⁺ | 14 | — |
| minus MgCl₂ | <1 | NT |
| minus ATP | <1 | NT |
| minus dNTP's | <1 | NT |

Reactions utilizing covalently closed G-T heteroduplex (modification on c strand) were performed as described in the legend to TABLE 2 except that 1.8 ng of exonuclease I was used. Repair of open circular DNA was performed in a similar manner except that MutH, DNA ligase, and β-AND⁺ were omitted from all reactions, and the hemimethylated G-T heteroduplex (modification on c strand) had been incised with MutH protein as described in the legend to FIG. 4. When present, rabb it antiserum to helicase II or pre-immune serum (5 μg protein) was incubated at 0° C. for 20 minutes with reaction mixtures lacking MgCl₂; the cofactor was then added and the assay was performed as above. Although not shown, antiserum inhibition was reversed by the subsequent addition of more helicase II. With the exception of the DNA polymerase III preparation, which contained about 15% by weight DNA helicase II (text), the purity of individual protein fractions was ≧95%. NT -- not tested.

These findings are in accord with previous conclusions concerning requirements of the methyl-directed reaction. However, in contrast to observations in vivo and in crude extracts indicating a requirement for the uvrD product, the reconstituted reaction proceeded readily in the absence of the added DNA helicase II (Table 2). Nevertheless, the reaction was abolished by antiserum to homogeneous helicase II, suggesting a requirement for this activity and that it might be present as a contaminant in one of the other proteins. Analysis of these preparations for their ability to restore mismatch repair to an extract derived from a uvrD (mutU) mutant and for the physical presence of helicase II by immunoblot assay revealed that the DNA polymerase III holoenzyme preparation contained sufficient helicase II (13 to 15 per cent of total protein by weight) to account for the levels of mismatch correction observed in the defined system. Similar results were obtained with holoenzyme preparations obtained from two other laboratories. The purified system therefore requires all the proteins that have been previously implicated in methyl-directed repair.

Figure 2:
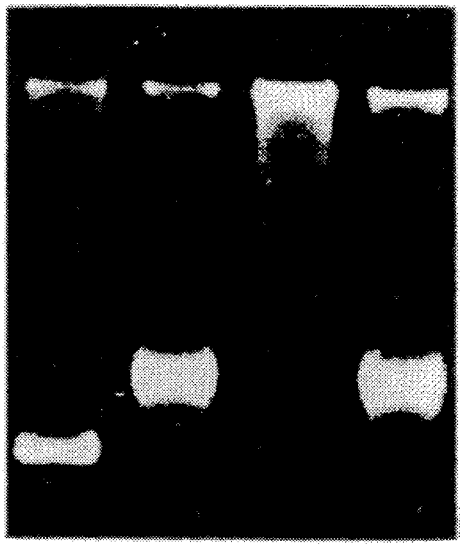
FIG. 2. Requirement for DNA ligase in mismatch correction. Hemimethylated G-T heteroduplex DNA [FIG. 1, 0.6 μg, d(GATC) methylation on the complementary DNA strand] was subjected to mismatch repair under reconstituted conditions in a 60 μl reaction (Table 3, closed circular heteroduplex), or in 20 μl reactions (0.2 μg of DNA) lacking MutS protein or ligase, or lacking both activities. A portion of each reaction (0.1 μg of DNA) was treated with EDTA (10 mM final concentration) and subjected to agarose gel electrophoresis in the presence of ethidium bromide (1.5 μg/ml; top panel, lanes 1–4). Positions are indicated for the unreacted, supercoiled substrate (SC), open circles containing a strand break (OC) and covalently closed, relaxed circular molecules (RC). A second sample of each reaction containing 0.1 μg of DNA was hydrolyzed with Xho I and Cla I endonucleases (FIG. 1) to score G-T→G-C mismatch correction and subjected to electrophoresis in parallel with the samples described above (bottom panel, lanes 5–8). The remainder of the complete reaction (0.4 μg DNA, corresponding to the sample analyzed in lane 1) was made 10 mM in EDTA, and subjected to electrophoresis as described above. A gel slice containing closed circular, relaxed molecules was excised and the DNA eluted. This sample was cleaved with Xho I and Cla I and the products analyzed by electrophoresis (lane 9).
Figure 2:
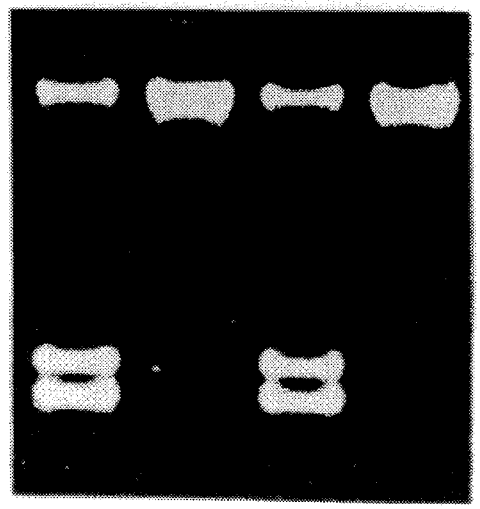
Figure 2:

The rate of correction of the closed circular heteroduplex was unaffected by omission of DNA ligase (Table 3), but the presence of this activity results in production of a covalently closed product. Incubation of a hemimethylated, supercoiled G-T heteroduplex with all seven proteins required for correction in the presence of DNA ligase resulted in extensive formation of covalently closed, relaxed, circular molecules. Production of the relaxed DNA was dependent on MutS (FIG. 2) and MutL proteins, and the generation of this species was associated with heteroduplex repair (FIG. 2). Correction also occurred in the absence of ligase, but in this case repair products were open circular molecules, the formation of which depended on the presence of MutS (FIG. 2). Since MutS has no known endonuclease activity but does recognize mispairs, it is inferred that open circular molecules are the immediate product of a mismatch-provoked excision repair process. Ligase closure of the strand break(s) present in this species would yield the covalently closed, relaxed circular product observed with the complete system.

The set of purified activities identified here as being important in methyl-directed repair support efficient correction. In the experiments summarized in Table 3, the individual proteins were used at the concentrations estimated to be present in the standard crude extract assay for correction as calculated from known specific activity determinations. Under such conditions the rate and extent of mismatch repair in the purified system are essentially identical to those observed in cell-free extracts.

Figure 3:
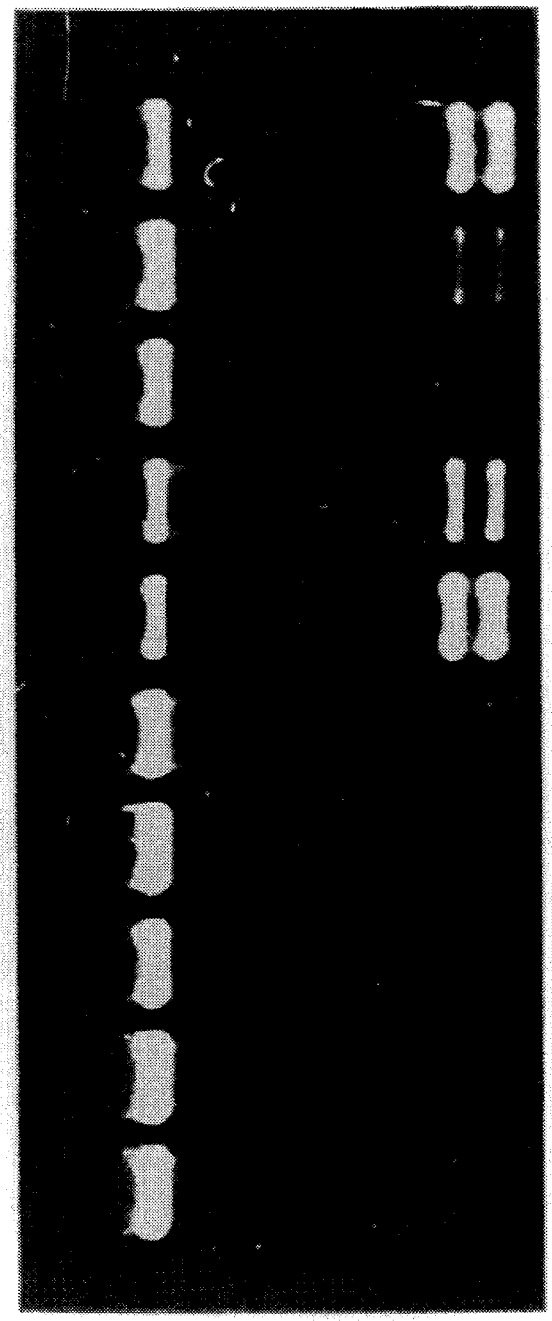
FIG. 3. Methyl-direction of mismatch correction in the purified system. Repair reactions with the G-T heteroduplex (FIG. 1) were performed as described in Table 3 (closed circular heteroduplex) except that reaction volumes were 20 μl (0.2 μg of DNA) and the incubation period was 60 minutes. The reactions were heated to 55° for 10 minutes and each was divided into two portions to test strand specificity of repair. G-T→A-T mismatch correction, in which repair occurred on the complementary (c) DNA strand, was scored by cleavage with Hind III and Cla I endonucleases, while hydrolysis with Xho I and Cla I were used to detect G-T→G-C repair occurring on the viral (v) strand. Apart from the samples shown in the left two lanes, all heteroduplexes were identical except for the state of methylation of the single d(GATC) sequence at position 216 (FIG. 1). The state of modification of the two DNA strands at this site is indicated by + and − notation. The G-T heteroduplex used in the experiment shown in the left two lanes (designated 0/0) contains the sequence d(GATT) instead of d(GATC) at position 216, but is otherwise identical in sequence to the other substrates.

DNA sites involved in repair by the purified system. The single d(GATC) sequence within the G-T heteroduplex shown in FIG. 1 is located 1024 base pairs from the mispair. Despite the distance separating these two sites, correction of the mismatch by the purified system responded to the state of modification of the d(GATC) sequence as well as its presence within the heteroduplex (FIG. 3). A substrate bearing d(GATC) methylation on both DNA strands did not support mismatch repair nor did a related heteroduplex in which the d(GATC) sequence was replaced by d(GATT). However, each of the two hemimethylated heteroduplexes were subject to strand-specific correction, with repair in each case being restricted to the unmodified DNA strand. With a heteroduplex in which neither strand was methylated, some molecules were corrected on one strand, and some were corrected on the other. As can be seen, the hemimethylated heteroduplex bearing methylation on the complementary DNA strand was a better substrate than the alternative configuration in which modification was on the viral strand, with a similar preference for repair of the viral strand being evident with the substrate that was unmethylated on either strand. This set of responses of the purified system to the presence and state of modification of d(GATC) sites reproduce effects previously documented in vivo and in crude extract experiments (R. S. Lahue, S. -S. Su, P. Modrich, *Proc. Natl. Acad. Sci. USA* 84, 1482, 1987).

The efficiency of repair by the methyl-directed pathway depends not only on the nature of the mispair, but also on the sequence environment in which the mismatch is embedded (P. Modrich, *Ann. Rev. Biochem.* 56, 435, 1987). To assess the mismatch specificity of the purified system under conditions where sequence effects are minimized, a set of heteroduplexes were used in which the location and immediate sequence environment of each mispair are essentially identical (S. -S. Su, R. S. Lahue, K. G. Au, P. Modrich, *J. Biol. Chem.* 263, 6829, 1988). This analysis (Table 4) showed that the

TABLE 4

Correction Efficiencies for Different Mismatches.

| | | Methylation State | | | |
|---|---|---|---|---|---|
| | | C⁺V⁻ | | C⁻V⁺ | |
| Heteroduplex | Markers | Rate | Bias | Rate | Bias |
| C 5'-CTCGA G AGCTT | Xho I | 1.2 | >18 | 0.38 | >5 |
| V 3'-GAGCT T TCGAA | Hind III | | | | |
| C 5'-CTCGA G AGCTG | Xho I | 1.1 | >17 | 0.38 | >6 |
| V 3'-GAGCT G TCGAC | Pvu II | | | | |
| C 5'-ATCGA T AGCTT | Cla I | 1.0 | >16 | 0.24 | 3 |
| V 3'-TAGCT T TCGAA | Hind III | | | | |
| C 5'-ATCGA A AGCTT | Hind III | 0.88 | >20 | 0.20 | >7 |
| V 3'-TAGCT A TCGAA | Cla I | | | | |
| C 5'-CTCGA A AGCTT | Hind III | 0.61 | 17 | 0.28 | >5 |

TABLE 4-continued

Correction Efficiencies for Different Mismatches.

| Heteroduplex | Markers | Methylation State | | | |
|---|---|---|---|---|---|
| | | $C^+V^-$ | | $C^-V^+$ | |
| | | Rate | Bias | Rate | Bias |
| V 3'-GAGCT C TCGAA | Xho I | | | | |
| C 5'-GTCGA C AGCTT | Sal I | 0.60 | 12 | 0.23 | >4 |
| V 3'-CAGCT T TCGAA | Hind III | | | | |
| C 5'-GTCGA A AGCTT | Hind III | 0.44 | >13 | 0.21 | 5 |
| V 3'-CAGCT G TCGAA | Sal I | | | | |
| C 5'-CTCGA C AGCTG | Pvu II | 0.04 | NS | <0.04 | NS |
| V 3'-GAGCT C TCGAC | Xho I | | | | |

Correction of the eight possible base-base mispairs was tested with the set of covalently closed heteroduplexes described previously including the G-T substrate shown in FIG. 1. With the exception of the mispair and the variations shown at the fifth position on either side, all heteroduplexes were identical in sequence. Each DNA was tested in both hemimethylated configurations under complete reaction conditions (Table 3, closed circular heteroduplex) except that samples were removed at 5-minute intervals over a 20 minute period in order to obtain initial rates (fmol/min). c and v refer to complementary and viral DNA strands, and Bias indicates the relative efficiency of mismatch repair occurring on the two DNA strands (ratio of unmethylated to methylated) as determined 60 minutes after the reaction was started. NS - not significant. With the exception of the C-C heteroduplexes, repair in the absence of MutS protein was less than 20% (in most cases <10%) of that observed in its presence (not shown).

purified system is able to recognize and repair in a methyl-directed manner seven of the eight possible base-base mismatches, with C-C being the only mispair that was not subject to significant correction. Table 3 also shows that the seven corrected mismatches were not repaired with equal efficiency and that in the case of each heteroduplex, the hemimethylated configuration modified on the complementary DNA strand was a better substrate than the other configuration in which the methyl group was on the viral strand. These findings are in good agreement with patterns of repair observed with this set of heteroduplexes in *E. coli* extracts (Although the patterns of substrate activity observed in extracts and in the purified system are qualitatively identical, the magnitude of variation observed differs for the two systems. Hemimethylated heteroduplexes modified on the complementary DNA strand are better substrates in both systems, but in extracts such molecules are repaired at about twice the rate of molecules methylated on the viral strand. In the purified system these relative rates differ by factors of 2 to 4. A similar effect may also exist with respect to mismatch preference within a given hemimethylated family. Although neither system repairs C-C, the rates of repair of other mismatches vary by a factors of 1.5 to 2 in extracts but by factors of 2 to 3 in the defined system.).

Strand-specific repair directed by a DNA strand break. Early experiments on methyl-directed repair in *E. coli* extracts led to the proposal that the strand-specificity of the reaction resulted from endonucleolytic incision of an unmethylated DNA strand at a d(GATC) sequence. This idea was supported by the finding that purified MutH protein has an associated, but extremely weak d(GATC) endonuclease that is activated in a mismatch-dependent manner in a reaction requiring MutL, MutS, and ATP. The purified system has been used to explore this effect more completely.

Figure 4:
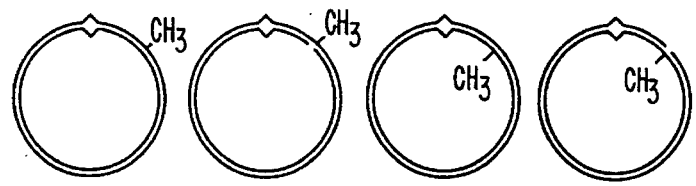
FIG. 4. Strand-specific repair of heteroduplexes containing a single strand scission in the absence of MutH protein. Hemimethylated G-T heteroduplex DNAs (FIG. 1, 5 μg) bearing d(GATC) modification on the viral or complementary strand were subjected to site-specific cleavage with near homogeneous MutH protein. Because the MutH-associated endonuclease is extremely weak in the absence of other mismatch repair proteins, cleavage at d(GATC) sites by the purified protein requires a MutH concentration 80 times that used in reconstitution reactions. After removal of MutH by phenol extraction, DNA was ethanol precipitated, collected by centrifugation, dried under vacuum, and resuspended in 10 mM Tris-HCl (pH 7.6), 1 mM EDTA. Mismatch correction of MutH-incised and covalently closed, control heteroduplexes was performed as described in the legend to Table 2 except that ligase and $NAD^+$ were omitted. Outside and inside strands of the heteroduplexes depicted here correspond to complementary and viral strands respectively. Values in parentheses indicate repair occurring on the methylated, continuous DNA strand. The absence of MutH protein in preparations of incised heteroduplexes was confirmed in two ways. Preparations of incised molecules were subject to closure by DNA ligase (>80%) demonstrating that MutH protein does not remain tightly bound to incised d(GATC) sites. Further, control experiments in which each MutH incised heteroduplex was mixed with a closed circular substrate showed that only the open circular form was repaired if MutH protein was omitted from the reaction whereas both substrates were corrected if MutH protein was present (data not shown).

The two hemimethylated forms of the G-T heteroduplex shown in FIG. 1 were incised using high concentrations of purified MutH protein to cleave the unmethylated DNA strand at the d(GATC) sequence (>>pGpApTpC). After removal of the protein, these open circular heteroduplexes were tested as substrates for the purified system in the absence of DNA ligase. Both open circular species were corrected in a strand-specific manner and at rates similar to those for the corresponding covalently closed heteroduplexes (FIG. 4). As observed with closed circular heteroduplexes, repair of the MutH-cleaved molecules required MutL, MutS, SSB, DNA polymerase III holoenzyme, and DNA helicase II (FIG. 4 and open circle entries of Table 2), but in contrast to the behavior of the closed circular substrates, repair of the mismatch within the open circular molecules occurred readily in the absence of MutH protein. Thus prior incision of the unmethylated strand of a d(GATC) site can bypass the requirement for MutH protein in strand-specific mismatch correction.

Figure 5:
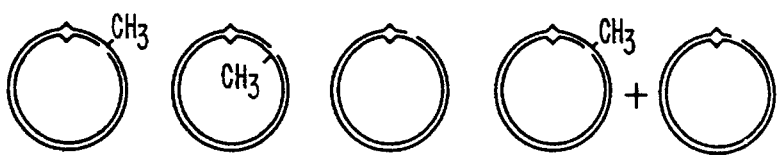
FIG. 5. Requirements for MutH protein and a d(GATC) sequence for correction in the presence of DNA ligase. Hemimethylated G-T heteroduplexes incised on the unmethylated strand at the d(GATC) sequence were prepared as described in the legend to FIG. 4. A G-T heteroduplex devoid of d(GATC) sites (FIG. 4) and containing a single-strand break within the complementary DNA strand at the Hinc II site (position 1) was constructed as described previously. Mismatch correction assays were performed as described in Table 3, with ligase (20 ng in the presence of 25 μM $NAD^+$) and MutH protein (0.26 ng) present as indicated. Table entries correspond to correction occurring on the incised DNA strand, with parenthetic values indicating the extent of repair on the continuous strand. Although not shown, repair of the nicked molecule lacking a d(GATC) sequence (first entry of column 3) was reduced more than an order of magnitude upon omission of MutL, MutS, SSB or DNA polymerase III holoenzyme.

The nature of the MutH-independent repair was examined further to assess the effect of ligase on the reaction and to determine whether a strand break at a sequence other than d(GATC) can direct correction in the absence of MutH protein (FIG. 5). As mentioned above, a covalently closed G-T heteroduplex that lacks a d(GATC) sequence is not subject to repair by the purified system in the presence (FIG. 3) or absence of DNA ligase. However, the presence of one strand-specific, site-specific break is sufficient to render this heteroduplex a substrate for the purified system in the absence of ligase and MutH protein (FIG. 5). Repair of this open circular heteroduplex was limited to the incised, complementary DNA strand, required presence of MutL and MutS proteins, DNA polymerase III, and SSB, and correction of the molecule was as efficient as that observed with the hemimethylated heteroduplex that had been cleaved by MutH at the d(GATC) sequence within the complementary strand. Although the presence of a strand break is sufficient to permit strand-specific correction of a heteroduplex in the absence of MutH and ligase, the presence of the latter activity inhibited repair not only on the heteroduplex lacking a d(GATC) sequence but also on both hemimethylated molecules that had been previously incised with MutH protein (FIG. 5). This inhibition by ligase was circumvented by the presence of MutH protein, but only if the substrate contained a d(GATC) sequence, with this effect being demonstrable when both types of heteroduplex were present in the same reaction (FIG. 5, last column). This finding proves that MutH protein recognizes d(GATC) sites and is consistent with the view that the function of this protein in mismatch correction is the incision of the unmethylated strand at this sequence.

EXAMPLE 2

Purification of MutY Protein

Purification of MutY Protein. *E. coli* RK1517 was grown at 37° C. in 170 liters of L broth containing 2.5 mM $KH_2PO_4$, 7.5 mM $Na_2HPO_4$ (culture pH=7.4) and 1% glucose. The culture was grown to an A590 of 4, chilled to 10° C. and cells were harvested by continuous flow centrifugation. Cell paste was stored at −70° C. A summary of the MutY purification is presented in Table 1. Fractionation procedures were performed at 0°–4° C., centrifugation was at 13,000×g, and glycerol concentrations are expressed as volume percent.

Frozen cell paste (290 g) was thawed at 4° C., resuspended in 900 ml of 0.05M Tris-HCl (pH 7.5), 0.1M NaCl, 1 mM dithiothreitol, 0.1 mM EDTA, and cells were disrupted by sonication. After clarification by centrifugation for 1 hr, the lysate (Fraction I, 970 ml) was treated with 185 ml of 25% streptomycin sulfate (wt/vol in 0.05M Tris-HCl (pH 7.5), 0.1M NaCl, 1 mM dithiothreitol, 0.1 mM EDTA) which was added slowly with stirring. After 30 min of additional stirring, the solution was centrifuged for 1 h, and the supernatant (1120 ml) was treated with 252 g of solid ammonium sulfate which was added slowly with stirring. After 30 min of additional stirring, the precipitate was collected by centrifugation for 1 h, resuspended to a final volume of 41 ml in 0.02M potassium phosphate (pH 7.5), 0.1 mM EDTA, 10% (vol/vol) glycerol, 1 mM dithiothreitol, and dialyzed against two 2 l portions of 0.02M potassium phosphate (pH 7.5), 0.1M KCl, 0.1 mM EDTA, 1 mM dithiothreitol, 10% glycerol (2 h per change). The dialyzed material was clarified by centrifugation for 10 min to yield Fraction II (45 ml).

Fraction II was diluted 10-fold into 0.02M potassium phosphate (pH 7.5), 0.1 mM EDTA, 1 mM dithiothreitol, 10% glycerol so that the conductivity of the diluted solution was comparable to that of the dilution buffer containing 0.1M KCl. The dilution was performed on small aliquots of Fraction II, and diluted samples were immediately loaded at 1 ml/min onto a 14.7 cm×12.6 cm² phosphocellulose column equilibrated with 0.02M potassium phosphate (pH 7.5), 0.1M KCl, 0.1 mM EDTA, 1 mM dithiothreitol, 10% glycerol. The column was washed with 400 ml of equilibration buffer, and developed with a 2 liter linear gradient of KCl (0.1 to 1.0M) in 0.02M potassium phosphate (pH 7.5), 0.1 mM EDTA, 1 mM dithiothreitol, 10% glycerol. Fractions containing MutY activity, which eluted at about 0.4M KCl, were pooled (Fraction III, 169 ml).

Fraction III was dialyzed against three 2 liter portions of 5 mM potassium phosphate (pH 7.5), 0.05M KCl, 0.1 mM EDTA, 1 mM dithiothreitol, 10% glycerol (2 h per change) until the conductivity was comparable to that of the dialysis buffer. After clarification by centrifugation at for 10 min, the solution was loaded at 0.5 ml/min onto a 21 cm×2.84 cm² hydroxylapatite column equilibrated with 5 mM potassium phosphate, pH 7.5, 0.05M KCl, 1 mM dithiothreitol, 10% glycerol. After washing with 130 ml of equilibration buffer, the column was eluted with a 600 ml linear gradient of potassium phosphate (5 mM to 0.4M, pH 7.5) containing 0.05M KCl, 1 mM dithiothreitol, 10% glycerol. Fractions eluting from the column were supplemented with EDTA to 0.1 mM. Peak fractions containing 60% of the total recovered activity, which eluted at about 0.1M potassium phosphate, were pooled (Fraction IV, 24 ml). The remaining side fractions contained impurities which could not be resolved from MutY by MonoS chromatography.

Fraction IV was diluted by addition of an equal volume of 0.05M KCl, 0.1 mM EDTA, 1 mM dithiothreitol, 10% glycerol. After clarification by centrifugation for 15 min, diluted Fraction IV was loaded at 0.75 ml/min onto a Pharmacia HR 5/5 MonoS FPLC column that was equilibrated with 0.05M sodium phosphate (pH 7.5), 0.1M NaCl, 0.1 mM EDTA, 0.5 mM dithiothreitol, 10% glycerol. The column was washed at 0.5 ml/min with 17 ml of equilibration buffer and developed at 0.5 ml/min with a

TABLE 1

Purification of MutY protein from 290 g of E. coli RK1517

| Fraction | Step | Total Protein mg | Specific Activity units/mg | Yield Percent |
|---|---|---|---|---|
| I | Extract | 10,900 | 40 | (100) |
| II | Ammonium sulfate | 1,350 | 272 | 84 |
| III | Phosphocellulose | 66 | 10,800 | 160 |
| IV | Hydroxylapatite | 1.4 | 136,000 | 44 |
| V | MonoS | 0.16 | 480,000 | 18 |

TABLE 1-continued

Purification of MutY protein from 290 g of E. coli RK1517

Specific A.G to C-G mismatch correction in cell-free extracts was determined as described previously (Au et al. 1988), except that ATP and glutathione were omitted from the reaction and incubation was for 30 min instead of 1 h. For complementation assays, each 0.01 ml reaction contained RK1517-Y33 extract (mutS mutY) at a concentration of 10 mg/ml protein. One unit of MutY activity is defined as the amount required to convert 1 fmol of A.G mismatch to C-G base pair per h under compleme ntation conditions.

20 ml linear gradient of NaCl (0.1 to 0.4M) in 0.05M sodium phosphate (pH 7.5), 0.1 mM EDTA, 0.5 mM dithiothreitol, 10% glycerol. Fractions with MutY activity, which eluted at approximately 0.2M NaCl, were pooled (Fraction V, 2.6 ml). Fraction V was divided into small aliquots and stored at $-70°$ C.

Assay for MutY-dependent, A.G-specific glycosylase

DNA restriction fragments were labeled at either the 3' or 5' ends with $^{32}$P. Glycosylase activity was then determined in 0.01 ml reactions containing 10 ng end-labeled DNA fragments, 0.02M Tris-HCl, pH 7.6, 1 mM EDTA, 0.05 mg/ml bovine serum albumin, and 2.7 ng MutY. After incubation at 37° C. for 30 min, the reaction mixture was treated with $2.5 \times 10^{-3}$ units of HeLa AP endonuclease II in the presence of 11 mM $MgCl_2$ and 0.005% Triton X-100 for 10 min at 37° C. Reactions were quenched by the addition of an equal volume of 80% formamide, 0.025% xylene cyanol, 0.025% bromphenol blue, heated to 80° C. for 2 min, and the products analyzed on an 8% sequencing gel. Control reactions contained either no MutY, no A.G mismatch or no AP endonuclease II.

Strand cleavage at the AP site generated by MutY could also be accomplished by treatment with piperidine instead of treatment with AP endonuclease II. After incubation for 30 min. at 37° C. with MutY as described above, the reaction mixture was precipitated with ethanol in the presence of carrier tRNA, then resuspended in 1M piperidine and heated at 90° C. for 30 min. After two additional ethanol precipitations, changing tubes each time, the pellet was resuspended in a minimum volume of water to which was added an equal volume of 80% formamide, 0.025% xylene cyanol, 0.025% bromphenol blue. The products were then analyzed on an 8% sequencing gel.

For purposes of completing the background description and present disclosure, each of the published articles, patents and patent applications heretofore identified in this specification are hereby incorporated by reference into the specification.

The foregoing invention has been described in some detail for purposes of clarity and understanding. It will also be obvious that various combinations in form and detail can be made without departing from the scope of the invention.

What is claimed is:

1. A method for detecting a base pair mismatch in a DNa duplex, comprising the steps of:

a) contacting a DNA duplex potentially containing a base pair mismatch with a protein that recognizes said base pair mismatch under conditions suitable for said protein to form a specific complex only with said DNA duplex having a base pair mismatch, and not with a DNA duplex lacking a base pair mismatch, and b) detecting any said complex as a measure of the presence of a base pair mismatch in said DNa duplex.

2. The method of claim 1 wherein said protein is the product of the mutS gene of *Escherichia coli*.

3. The method of claim 2 wherein said protein recognizes all eight possible base pair mismatches.

4. The method of claim 1 wherein said protein is the product of the mutY gene of *Escherichia coli*.

5. The method of claim 1 wherein said protein is a homolog of the MutS protein of *Escherichia coli*.

6. The method of claim 1 wherein said protein is a homolog of the MutY protein of *Escherichia coli*.

* * * * *